(12) United States Patent  (10) Patent No.: US 6,928,144 B2
Li et al.  (45) Date of Patent: Aug. 9, 2005

(54) GUARD RING FOR DIRECT PHOTO-TO-ELECTRON CONVERSION DETECTOR ARRAY

(75) Inventors: Wen Li, Clifton Park, NY (US); Jianguo Zhao, Fremont, CA (US)

(73) Assignee: General Electric Company, Niskayuna, NY (US)

( * ) Notice: Subject to any disclaimer, the term of this patent is extended or adjusted under 35 U.S.C. 154(b) by 88 days.

(21) Appl. No.: 10/633,119

(22) Filed: Aug. 1, 2003

(65) Prior Publication Data

US 2005/0023475 A1 Feb. 3, 2005

(51) Int. Cl.[7] .......................... H05G 1/64; H01L 31/00; G01T 1/24
(52) U.S. Cl. .................... 378/98.8; 378/19; 250/370.09
(58) Field of Search ............... 378/19, 98.8; 250/208.1, 250/370.01, 370.08, 370.09, 370.1

(56) References Cited

U.S. PATENT DOCUMENTS

| | | | |
|---|---|---|---|
| 4,864,378 A | | 9/1989 | Tsaur |
| 5,563,421 A | * | 10/1996 | Lee et al. .................... 250/580 |
| 5,905,264 A | * | 5/1999 | Shahar et al. ........... 250/370.01 |
| 6,034,373 A | * | 3/2000 | Shahar et al. ........... 250/370.01 |
| 6,066,884 A | | 5/2000 | Krutsick |
| 6,177,293 B1 | | 1/2001 | Netzer |
| 6,229,191 B1 | | 5/2001 | Cao |
| 6,380,528 B1 | * | 4/2002 | Pyyhtia et al. ........... 250/208.1 |
| 6,399,413 B1 | | 6/2002 | Krutsick |
| 6,465,824 B1 | | 10/2002 | Kwasnick |
| 6,504,158 B2 | | 1/2003 | Possin |
| 6,504,904 B2 | | 1/2003 | Danielsson |
| 6,545,711 B1 | * | 4/2003 | Perner et al. ................ 348/294 |
| 6,583,482 B2 | | 6/2003 | Pauchard |

* cited by examiner

*Primary Examiner*—Allen C. Ho
(74) *Attorney, Agent, or Firm*—Jean K. Testa; Patrick K. Patnode

(57) ABSTRACT

A device for use in an imaging system is provided including a direct conversion detector element configured to convert x-ray photons into electric current. The direct conversion detector element is comprised of a cathode surface, an anode surface having a plurality of anode side edges, and a plurality of detector side surfaces connecting the cathode surface to the anode surface. The plurality of detector side surfaces each have a detector depth. The device further includes a pixel array assembly positioned on the anode surface. The pixel array assembly includes a plurality of pixel side edges. Each of the plurality of pixel side edges is immediately adjacent one of the anode side edges. A guard ring is mounted around the plurality of detector side surfaces. The guard ring includes an upper ring edge, a lower ring edge, and a ring outer surface including a guard ring height.

19 Claims, 3 Drawing Sheets

GUARD RING FOR DIRECT PHOTO-TO-ELECTRON CONVERSION DETECTOR ARRAY

TECHNICAL FIELD

The present invention relates generally to detector elements for use in medical imaging, and more particularly, to direct conversion detector arrays for use in medical imaging.

BACKGROUND OF THE INVENTION

Direct conversion detectors and detector arrays are utilized in medical imaging in order to convert x-ray photons directly into electric charges. They are typically comprised of an x-ray photoconductor layer grown directly on top of the charge collector and readout layer (such as room temperature semi-conductors). The detectors are commonly utilized in arrays of multiple detector (or tiles) such that an increased image size with improved resolution may be generated.

The performance of the detectors, especially the peripheral detector elements, can be important to many imaging applications. The linearity, uniformity, stability, and consistency can be especially important for peripheral detectors. For many applications, such as mammography chest wall dead space, the requirements of imaging can be very stringent. For tiled imaging detectors built with room temperature semiconductors, the edges of each tile can cause significant non-uniformity or visible artifacts. This is known to arise due to the much higher leakage current and distorted electric field near the edges. Artifacts around the edges of the tiles may be highly undesirable. These artifacts are believed to be caused by the degraded performance of the edge pixels. These artifacts become roadblocks for the implementation of these detectors and detector arrays in medical imaging applications where line artifacts are prohibited.

It is known that a guard ring may be utilized to improve peripheral pixel behavior. Know configurations manufacture the guard ring on the same surface of the pixellated side of the detector and apply the same potential as its neighbor, i.e. ground. Therefore, the electric field distortion to the edge pixels is reduced or eliminated depending on the size of the guard ring. Furthermore, side wall leakage current is collected by the guard ring and has no impact on the edge pixels. However, these co-planar guard rings generate an inactive spatial region with a dimension of the guard ring geometry. This is undesirably for tiled detector boundaries or detector edges which can have a very limited tolerance to inactive space. Thus existing guard ring designs may also be unsuitable for medical imaging applications wherein line artifacts due to the inactive space may be unacceptable.

It would, therefore, be highly desirable to have a direct conversion detector with improved edge pixel performance. It would additionally be highly desirable to have a direct conversion detector array with reduced artifacts and reduced inactive space characteristics.

SUMMARY OF THE INVENTION

A device for use in an imaging system is provided including a direct conversion detector element configured to convert x-ray photons into electric current. The direct conversion detector element is comprised of a cathode surface, an anode surface having a plurality of anode side edges, and a plurality of detector side surfaces connecting the cathode surface to the anode surface. The plurality of detector side surfaces each have a detector depth. The device further includes a pixel array assembly positioned on the anode surface. The pixel array assembly includes a plurality of pixel side edges. Each of the plurality of pixel side edges is immediately adjacent one of the anode side edges. A guard ring is mounted around the plurality of detector side surfaces. The guard ring includes an upper ring edge, a lower ring edge, and a ring outer surface including a guard ring height.

Other features of the present invention will become apparent when viewed in light of the detailed description of the preferred embodiment when taken in conjunction with the attached drawings and appended claims.

DESCRIPTION OF THE PREFERRED EMBODIMENT(S)

Figure 1:
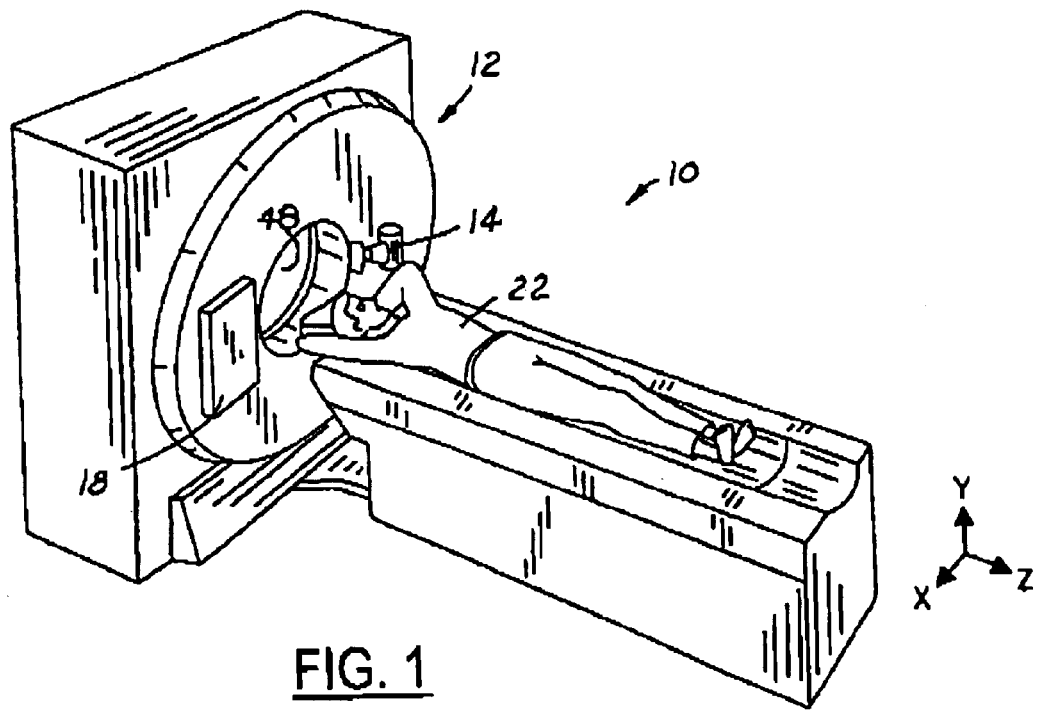
FIG. 1 is an illustration of a medical imaging system in accordance with one embodiment of the present invention.
Figure 2:
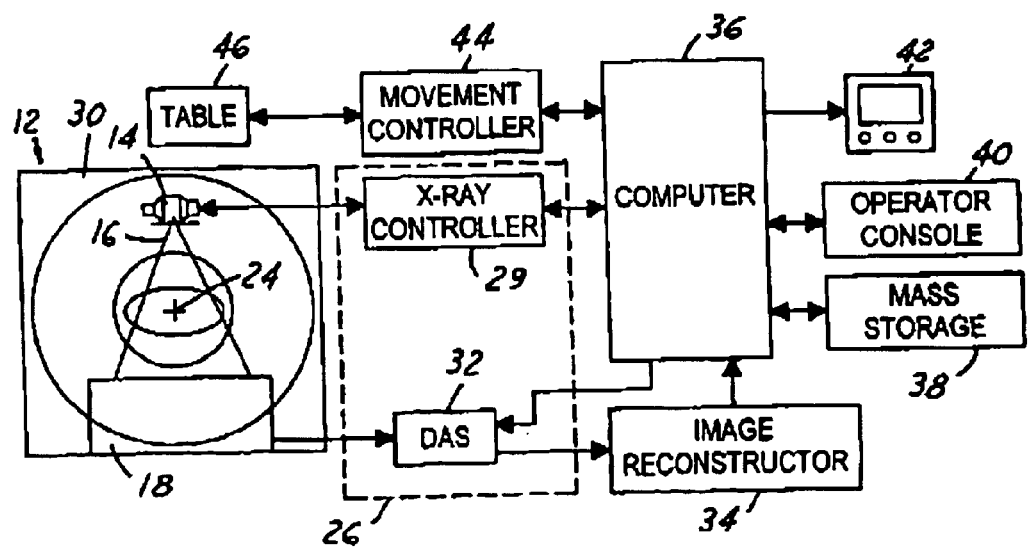
FIG. 2 is an illustration of the medical imaging system illustrated in FIG. 1.
Figure 3:
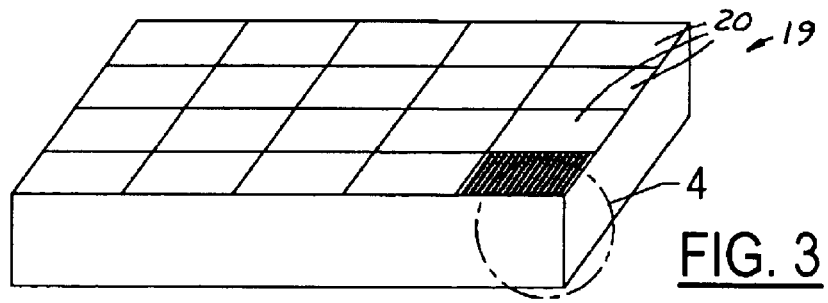
FIG. 3 is an illustration of a detector array in accordance with the present invention.

Referring now to FIG. 1, which is an illustration of a computed tomography (CT) imaging system 10 for use with the detector assembly 18 of the present invention. Although a particular CT imaging system 10 has been illustrated, it should be understood that the detector assembly 18 of the present invention can be utilized in a wide variety of imaging systems. The CT imaging system 10 includes a scanner assembly 12 illustrated as a gantry assembly. The scanner assembly 12 includes an x-ray source 14 for projecting a beam of x-rays 16 toward a detector assembly 18 positioned opposite the x-ray source 14. The detector assembly 18 includes a direct conversion detector array 19 comprised of a plurality of direct conversion detector elements 20 (see FIG. 3) which combine to sense the projected x-ray photons 16 that pass through an object, such as a medical patient 22. Each of the plurality of direct conversion detector elements 20 produces an electrical signal that represents the intensity of an impinging x-ray beam and hence the attenuation of the beam 16 as it passes through the object of patient 22. Commonly, during a scan to acquire x-ray projection data, the scanner assembly 12 is rotated about the center of rotation 24. The direct conversion detector elements 20 are preferably arranged in detector array 19, such that projection data corresponding to a plurality of parallel slices can be acquired simultaneously during a scan.

The rotation of the scanner assembly 12 and the operation of the x-ray source 14 are preferably governed by a control mechanism 26. The control mechanism 26 preferably includes an x-ray controller 29 that provides power and timing signals to the x-ray source 14 and a scanner motor controller 30 that controls the rotational speed and position of the scanner assembly 12. A data acquisition system (DAS)

32 in control mechanism 26 samples analog data from the direct conversion detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

The computer 36 also can receive commands and scanning parameters from an operator via console 40 that has a keyboard or similar input device. An associated display 42 allows the operator to observe the reconstructed image and other data from the computer 36. The operator supplied commands and parameters are used by computer 36 to provide control signals and information to the DAS 32, x-ray controller 29, and scanner motor controller 30. In addition, the computer 36 operates a table motor controller 44 which controls a motorized table 46 to position patient 22 within the scanner assembly 12. Particularly, the table 46 moves portions of the patient 22 through the scanner opening 48.

Figure 4:
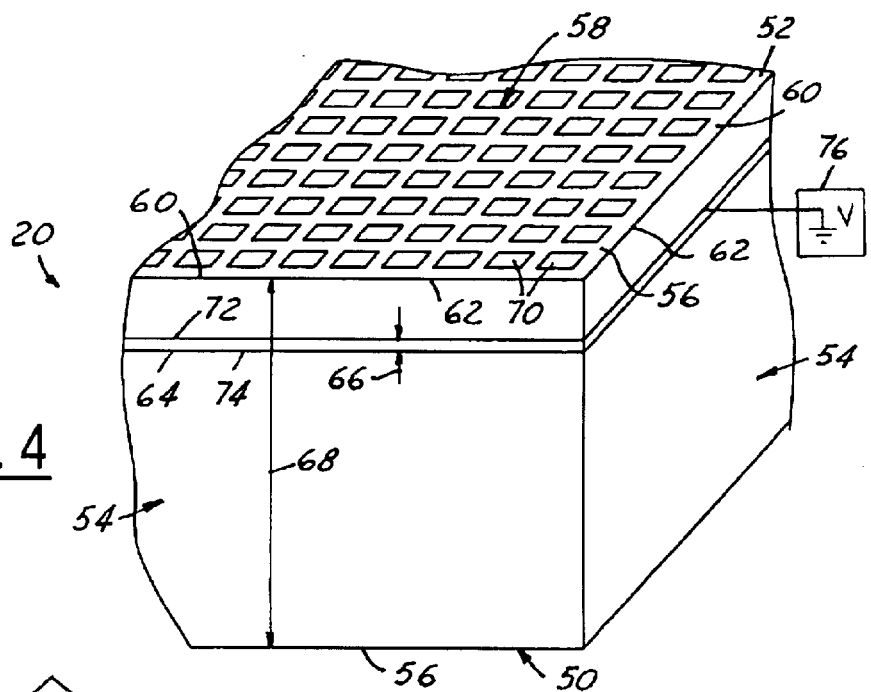
FIG. 4 is a detailed illustration of a direct conversion detector array in accordance with the present invention.

A detail of one of the direct conversion detector elements 20 from the detector array 19 is illustrated in FIG. 4. The direct conversion detector element 20 is preferably a semiconductor material (such as CdTe/CdZnTe) having of a cathode surface 50, an anode surface 52, and a plurality of detector side surfaces 54. The cathode surface 50 and the anode surface 52 are coated with a metal material 56 to act as electrodes. A pixel array assembly 58 is coated on the anode surface 52. The electrode surfaces 50,52 are biased with different voltages to create an electric field across the direct conversion detector element 20. When a negative high voltage is applied to the cathode surface 50 and the pixel array assembly 58 on the anode surface 52 is connected to a ground or virtual ground, electric signals due to motion of electrons generated inside the direct conversion detector element 20 by the x-ray photons 16 can be collected/observed. Through different electric field voltages applied to the anode surface 52 and cathode surface 50, holes can be collected/observed. The pixel array assembly 58 includes a plurality of pixel side edges 60. The pixel side edges 60 preferably are immediately adjacent the anode side edges 62 such that dead space within the detector array 19 is minimized.

Figure 5:
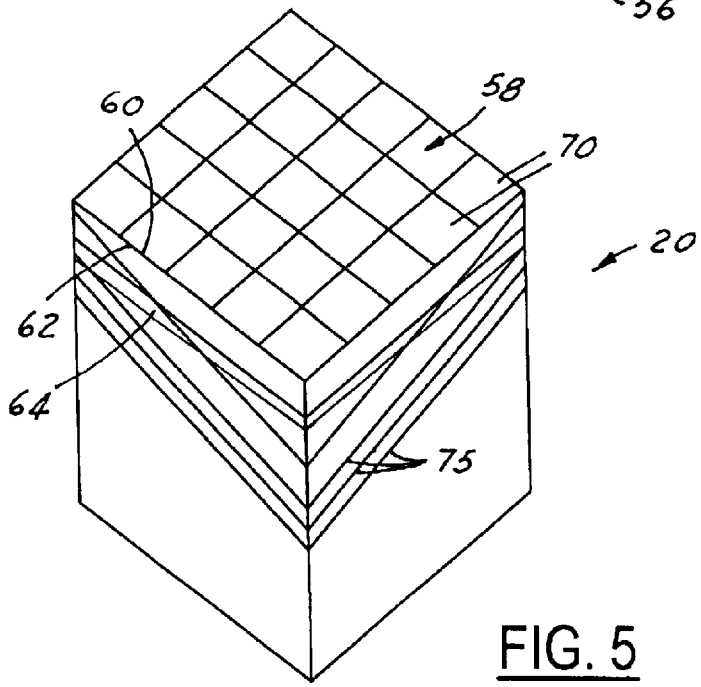
FIG. 5 is a detailed illustration of the direct conversion detector array illustrated in FIG. 4, the detail illustrating detector geometry and electric field/potential distribution.

The present invention further includes a guard ring 64 coated/deposited on the detector side surfaces 54. Although the guard ring 64 may be comprised of a variety of materials, in one embodiment it is contemplated that the guard ring 64 is comprised of the same materials as the electrodes 50,52 such as Au or Pt. The guard ring 64 is electrically connected to the detector side surfaces 54 where it overlaps. The guard ring 64 includes a guard ring height 66 which is smaller than the detector depth 68. The guard ring 64 may be positioned at a variety of positions along the detector depth 68 to optimize perimeter pixel 70 performance. Similarly, the guard ring height 66 can be adjusted to optimize perimeter pixel 70 performance. The guard ring height 66 is defined between a upper ring edge 72 and a lower ring edge 74. In one embodiment, the upper ring edge 72 and the lower ring edge 74 are positioned closer to the anode surface 52 than the cathode surface 50. By way of example, FIG. 5 illustrated an embodiment of a direct conversion detector element 20. The direct conversion detector element 20 is 0.5×0.5×1 mm$^3$ pixelated crystal. The CdZnTe crystal is fabricated with a 5×5 pixel array 58 with a pixel pitch of 100 um. The guard ring 64 is positioned 0.1 mm from the anode surface 52 and has a guard ring height of 0.01 mm. The cathode surface 50 is biased with −400 volts and the anode surface 52 are grounded (0 V). The simulated field/potential distribution 75 is illustrated on the detector side surfaces 54.

Figure 6A:
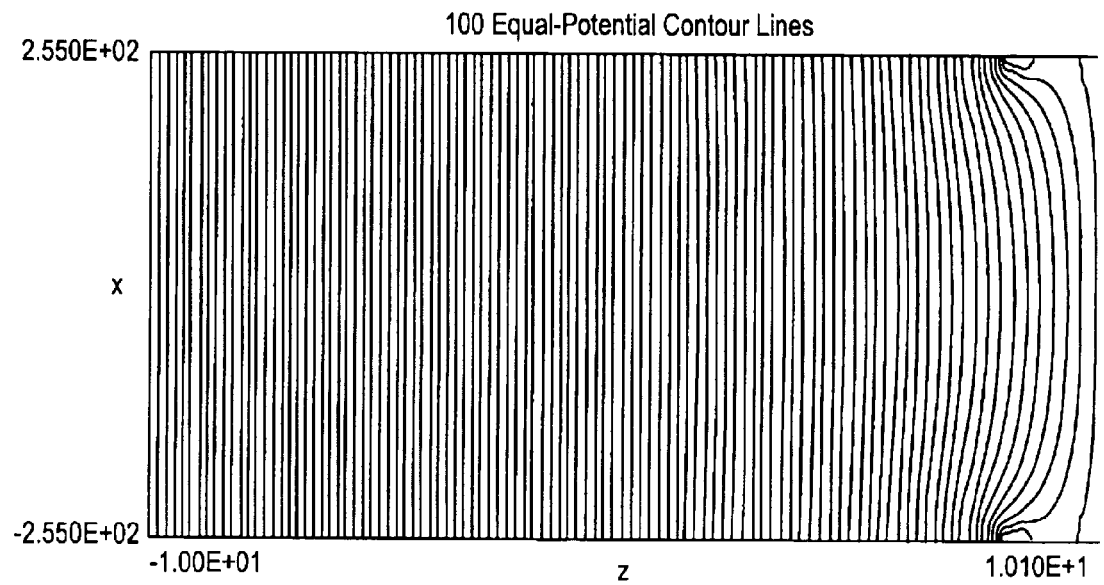
FIG. 6a is a graph of simulated electric potential distrubution with a zero voltage bias.
Figure 6B:
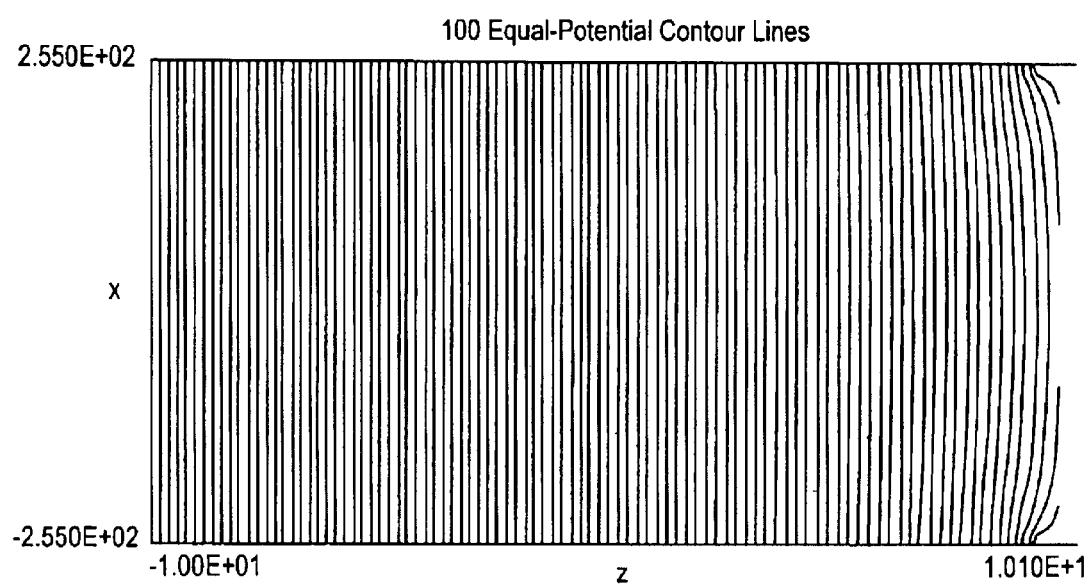
FIG. 6b is a graph of simulated electric potential distribution with a 20 volt voltage bias.

The guard ring 64 can further be connected to a voltage source 76 such that a bias voltage can be imparted to the guard ring 64. The bias voltage can be different from the bias of the two electrodes 50,52 or can be the same as one of the electrodes 50,52. The voltage source 76 can be utilized to adjust the bias voltage to further optimize the performance of the peripheral pixels 70. FIGS. 6a and 6b are graphical illustrations of the potential distributions plotted against equal-potential contour lines. The predictive calculations demonstrate the benefits of properly calculating the bias voltage for the guard ring 64. FIG. 6a illustrates a zero bias while FIG. 6b illustrates a −20V bias. The higher bias in FIG. 6a illustrates improvements in electric field uniformity but leakage voltage between the guard ring 64 and peripheral pixels 70 increased. With the −20V bias in FIG. 6b, the leakage current between the guard ring 64 and peripheral pixels 70 is improved. It should be understood that these predictive results are illustrative only, and bias for the guard ring 64 needs to be optimized according to the geometry and material properties of the direct conversion detector element 20.

While particular embodiments of the invention have been shown and described, numerous variations and alternative embodiments will occur to those skilled in the art. Accordingly, it is intended that the invention be limited only in terms of the appended claims.

What is claimed is:

1. A device for use in an imaging system comprising:
   a direct conversion detector element configured to convert x-ray photons into electric current, said direct conversion detector element comprising:
   a cathode surface;
   an anode surface having a plurality of anode side edges; and
   a plurality of detector side surfaces connecting said cathode surface to said anode surface, said plurality of detector side surfaces each having a detector depth;
   a pixel array assembly positioned on said anode surface, said pixel array assembly including a plurality of pixel side edges, each of said plurality of pixel side edges immediately adjacent one of said anode side edges;
   a guard ring mounted around said plurality of detector side surfaces, said guard ring including an upper ring edge, a lower ring edge, and a ring outer surface including a guard ring height, wherein said ring outer surface is coplanar with said plurality of detector side surfaces.

2. A device as in claim 1 further comprising:
   a voltage source in communication with said guard ring, said voltage source biasing said guard ring with a bias voltage.

3. A device as in claim 1 wherein said upper ring edge and said lower ring edge are remotely positioned from said cathode surface and said anode surface.

4. A device as in claim 1 wherein said ring outer surface is coplanar with said pixel side edges.

5. A device as in claim 1 wherein said direct conversion detector element comprises amorphous selenium.

6. A device as in claim 1 wherein said pixel assembly comprises a room temperature semiconductor.

7. A device as in claim 1 wherein said direct conversion detector element comprises a CdTe detector.

8. A device as in claim 1 wherein guard ring height is 50% or less of said detector depth.

9. A device as in claim 1 wherein said upper ring edge and said lower ring edge are positioned closer to said anode surface than said cathode surface.

10. An imaging system comprising:

an x-ray source;

a detector array comprising a plurality of direct conversion detector elements configured to convert x-ray photons into electric current, each of said plurality of direct conversion detector elements comprising:

a cathode surface;

an anode surface having a plurality of anode side edges; and a plurality of detector side surfaces connecting said cathode surface to said anode surface, said plurality of detector side surfaces each having a detector depth;

a pixel array assembly positioned on said anode surface, said pixel array assembly including a plurality of pixel side edges;

a guard ring mounted around said plurality of detector side surfaces, said guard ring including an upper ring edge, a lower ring edge, and a ring outer surface including a guard ring height, said ring outer surface positioned coplanar with said pixel side edges.

11. An imaging system as described in claim 10 wherein each of said plurality of pixel side edges is positioned immediately adjacent one of said anode side edges.

12. An imaging system as in claim 10 further comprising:

a voltage source in communication with said guard ring, said voltage source biasing said guard ring with a bias voltage.

13. An imaging system as in claim 10 wherein said upper ring edge and said lower ring edge are remotely positioned from said cathode surface and said anode surface.

14. An imaging system as in claim 10, wherein said ring outer surface is coplanar with said plurality of detector side surfaces.

15. An imaging system as in claim 10 wherein said guard ring is coated on said plurality of detector side surfaces such that said guard ring is substantially coplanar with said plurality of detector side surfaces.

16. A method of improving the performance of peripheral pixel elements positioned on an anode surface of a direct conversion detector element, the direct conversion detector element having a cathode surface and a plurality of detector side surfaces, comprising:

applying a guard ring around said plurality of detector side surfaces, said guard ring applied coplanar to said peripheral pixel elements such that a ring outer surface of said guard ring is coplanar with said plurality of detector side surfaces.

17. A method as described in claim 16, further comprising:

applying a bias voltage to said guard ring.

18. A method as described in claim 16, further comprising:

adjusting a guard ring height of said guard ring to maximize the performance of the peripheral pixel elements.

19. A method as described in claim 16, further comprising:

adjusting a guard ring position along a detector depth to maximize the performance of the peripheral pixel elements.

* * * * *